(12) United States Patent
Chandra et al.

(10) Patent No.: US 7,385,101 B2
(45) Date of Patent: Jun. 10, 2008

(54) ANTIBIOTIC TEXTILE MATERIALS SUITABLE FOR WOUND DRESSINGS AND WOUND DRESSINGS INCORPORATING THE SAME

(75) Inventors: Satish N. Chandra, Lansdale, PA (US); Joel M. Furey, Stowe, VT (US); William Francis McNally, Clark Summit, PA (US)

(73) Assignee: Noble Fiber Technologies, LLC, Scranton, PA (US)

( * ) Notice: Subject to any disclaimer, the term of this patent is extended or adjusted under 35 U.S.C. 154(b) by 765 days.

(21) Appl. No.: 10/325,419

(22) Filed: Dec. 20, 2002

(65) Prior Publication Data

US 2003/0176827 A1  Sep. 18, 2003

Related U.S. Application Data

(60) Provisional application No. 60/412,214, filed on Sep. 20, 2002, provisional application No. 60/344,309, filed on Dec. 20, 2001.

(51) Int. Cl.
*A61F 13/00* (2006.01)

(52) U.S. Cl. ............................. 602/48; 602/42; 602/43; 602/45

(58) Field of Classification Search ............ 602/41–59; 604/304–308; 424/443–449, 405, 618; 514/179, 514/192, 199, 535; 128/888, 889
See application file for complete search history.

(56) References Cited

U.S. PATENT DOCUMENTS

| | | | | |
|---|---|---|---|---|
| 3,670,731 A | * | 6/1972 | Harmon ................... 604/368 |
| 6,087,549 A | * | 7/2000 | Flick ............................. 602/41 |
| 6,362,387 B1 | * | 3/2002 | Carlson et al. ............... 602/41 |
| 6,861,570 B1 | | 3/2005 | Flick | |
| 2003/0180346 A1 | * | 9/2003 | Woods ........................ 424/446 |
| 2004/0049145 A1 | * | 3/2004 | Flick ............................ 602/41 |
| 2004/0241213 A1 | | 12/2004 | Bray | |
| 2005/0244484 A1 | * | 11/2005 | Flick .......................... 424/445 |

FOREIGN PATENT DOCUMENTS

| | | |
|---|---|---|
| EP | 0128338 A1 | 12/1984 |
| EP | 0291587 A1 | 11/1988 |
| EP | 0344090 A2 | 11/1989 |
| EP | 0392640 A2 | 10/1990 |
| EP | 0354315 A1 | 5/1992 |
| EP | 1 882 482 A2 | 1/2008 |
| GB | 942193 | 11/1963 |
| GB | 2092006 | 8/1982 |
| JP | 4202849 | 7/1992 |
| WO | WO 90/08470 | 8/1990 |
| WO | WO 91/11206 | 8/1991 |
| WO | WO 92/13491 | 8/1992 |
| WO | 0025726 | 5/2000 |

* cited by examiner

*Primary Examiner*—Kim M Lewis
(74) *Attorney, Agent, or Firm*—Akerman Senterfitt; Michael K. Dixon

(57) ABSTRACT

A hydrophilic textile matrix having antibiotic activity is provided. The textile matrix is a non-woven material including a blend (i.e., mixture) of metallic silver-coated fibers and a non-metallic, water absorbent material. Wound dressings incorporating the textile matrices are provided.

33 Claims, 1 Drawing Sheet

500 # ANTIBIOTIC TEXTILE MATERIALS SUITABLE FOR WOUND DRESSINGS AND WOUND DRESSINGS INCORPORATING THE SAME

This application claims priority under 35 U.S.C. §119(e) from Provisional Application Nos. 60/412,214, filed Sep. 20, 2002 and 60/344,309, filed Dec. 20, 2001, both of which are herein incorporated by reference.

FIELD OF THE INVENTION

The present invention relates to antibiotic, absorbent textile materials particularly suitable for wound dressings, and more particularly to non-woven, absorbent textile materials including metallic silver-coated fibers.

BACKGROUND OF THE INVENTION

The use of metallic silver as an antimicrobial has been known since ancient times. In recent years, a renewed interest has developed in the use of metallic silver as an antibiotic especially in wound dressings. This renewed interest is driven in part by the development of antibiotic-resistant bacteria, such as methicillin-resistant *Staphylococcus aureus* (MRSA). Antibiotic-resistant bacteria are especially problematic since an increasing number of commonly used antibiotics are becoming ineffective. Metallic silver, which release ionic silver into the wound, is a broad-spectrum antibiotic that has been found particular effective against such resistant bacterial strains. Moreover, bacteria do not appear to develop resistance to silver as compared to conventional antibiotics.

Metallic silver is also known to exhibit wound-healing properties. Expeditious wound healing benefits the patient in terms of increased comfort and decreased susceptibility to infection and secondary injury. Examples of wound dressings incorporating metallic silver-coated fibers are those sold under the tradename Silverlon® from Argentum Medical LLC located in Roswell, Ga. Other examples of wound dressings incorporating metallic silver-coated fibers are described in U.S. Pat. No. 6,087,549 also assigned to Argentum Medical LLC.

Although metallic silver has distinct advantages, silver primarily used for wound dressings is in an ionic form (i.e., a silver salt or compound). However, the antibiotic activity provided with ionic silver from silver salts or compounds dissipate rather quickly due to the silver salts or compounds in the wound care product being dissolved by the aqueous nature of the wound environment. As a result, dressings must be replaced frequently resulting in pain or discomfort and inconvenience for the patient as the dressing is removed and replaced. Moreover, the rapid release of ionic silver can possibly lead to toxicity. Similarly, silver-containing creams (e.g., including silver sulfadiazine) must be consistently reapplied to the injured area, and the dressing must be removed for reapplication of the cream. Silver salts, as well as unbound metallic silver particles, can also irritate the skin and prolonged contact can cause localized or site-specific argyria, which is characterized by a pronounced, permanent ashen-gray skin discoloration.

As is well known in the art, a moist environment promotes wound healing. Thus, would dressings often include hydrophilic (i.e., water-absorbent) fibrous materials to maintain moisture at the wound site. One class of water-absorbent materials is alginates, which are fibrous products derived from seaweed, and is commonly used to facilitate a moist wound environment. However, a moist environment also facilitates the growth of bacteria, which slows wound healing, causes unpleasant odors and can eventually lead to serious and life-threatening infections. While bandages including water-absorbent materials (e.g., calcium alginate) help to maintain a moist wound environment, they have been known to cause adherence of the dressing to the wound site. Adherence of the wound dressing causes pain and discomfort to the patient and lengthens the time required for changing the dressing and the time required for a wound to heal.

Attempts to obviate bacterial growth in water-absorbent materials have included the incorporation of antibiotics. Metallic silver-coated fibers are not used due to their hydrophobic nature, which renders them incompatible for use with water-absorbent fibers such as calcium alginate. Thus, attempts to prepare fibrous mixtures of silver-coated fibers for wound dressings generally entail using hydrophobic fibrous materials such as polyethylene and the like as taught in U.S. Pat. No. 6,087,549.

In view of the above, it is clearly apparent that there are deficiencies with currently available wound dressings. First, there is a need for antibiotic wound dressings that use metallic silver to inhibit the growth of MSRA and other antibiotic-resistant bacteria. There is also a need for wound care products that releases silver ions over an extended period of time which alleviates the need for frequent removal or replacement of the dressing or application of silver creams. There is also a need for wound dressings that maintain a moist wound environment but reduces physical adherence to the wound site. Likewise, there is a need for wound dressings that maintain a moist wound-healing environment while inhibiting bacterial growth. Likewise, there is a need for non-irritating silver wound dressings that obviate the need of silver salts for the delivery of silver ions thereby eliminating the potential development of argyria.

SUMMARY OF THE INVENTION

In view of the above, the present invention provides a hydrophilic textile matrix having antibiotic activity that advantageously provides sustained ionic silver delivery along with moist environment for wound healing. The matrix of the present invention is a non-woven material including a blend of metallic silver-coated fibers and a non-metallic, water-absorbent material. In one preferred embodiment, the non-metallic, water-absorbent material is in the form of fibers or a hydrogel. In another embodiment, the textile matrix has a water absorption of at least 10 grams per gram of matrix. The non-metallic, water-absorbent material is preferably a polysaccharide material such as a hydrocolloid with an alginate or derivative thereof being especially preferred. One preferred alginate is calcium alginate or a derivative thereof. The metallic silver-coated fibers incorporated in the textile matrix preferably are 0.5 to 50 denier per filament. A preferred blend for the textile matrix is about 1 to about 80 percent by weight of the metallic silver-coated fibers and about 10 to about 80 percent by weight of the non-metallic, water-absorbent fibers.

In another embodiment, the present invention provides a wound dressing including a substantially planar and flexible backing material and a layer of a hydrophilic textile matrix having anti-microbial activity disposed on one side of said backing material. The matrix as described above matrix is a non-woven material including a blend of metallic silver-coated fibers and a non-metallic, water-absorbent material. Preferably, the backing layer of the wound dressing includes an adhesive layer disposed on the same side as the hydrophilic textile matrix but exclude the hydrophilic textile matrix.

The textile matrix of the present invention provides a unique combination of properties which previously were not available in wound dressings. These and other advantages of the invention will become more readily apparent from the description set forth below.

DETAILED DESCRIPTION OF THE INVENTION

Figure 1:
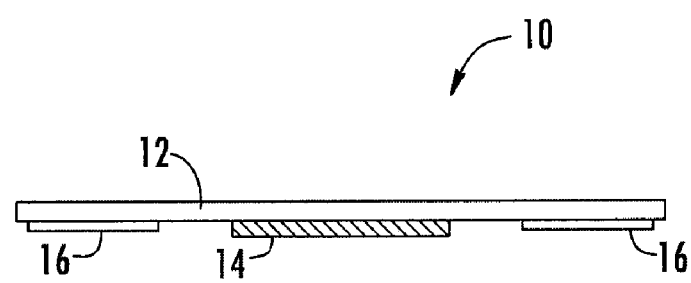
FIG. 1 is a cross-sectional view of a wound dressing in the form of a bandage incorporating the antibiotic textile matrix of the present invention.

The present invention provides an absorbent textile matrix having antibiotic activity, which is particularly useful for wound dressings. Reference to "absorbent" means that the matrix absorbs water or water-based media such as wound exudate which is primarily composed of water. The matrices of the invention include a blend (or mixture) of metallic silver-coated fibers and a non-metallic water-absorbent material. The textile matrices due to their antibiotic/antimicrobial properties in addition their absorptive properties render them especially useful in wound care products, such as wound dressings.

Metallic silver-coated fibers to be used in accordance with the invention are well known in the art. The metallic silver is preferably of high purity, which in the context of the invention means a purity of at least about 99.9%. The base materials for the fiber include any polymeric material such as polyolefins, polyamides, polyesters, polypropylenes, acrylics and combinations thereof. Polyamides are preferred with nylon being particularly preferred. Processes for producing metallic silver-coated fibers include electroplating, electroless plating, and vapor deposition among others. Commercial providers of metallic silver-coated fibers are Sauquoit Industries, Inc., Scranton, Pa., Marktek Inc., Chesterfiled, Mo., Monster Cable Products, Inc., Brisbane, Calif. and Alpha Wire Company, Elizabeth, N.J. Preferred metallic silver coated fibers are those manufactured as described in U.S. Pat. No. 4,042,737, entitled "Process for producing crimped metal-coated filamentary materials, and yarns and fabrics obtained therefrom," issued to Rohm and Haas Company (Philadelphia, Pa.). Such fibers are commercially available from Noble Fiber Technologies under the tradename X-Static®.

Preferably, the fibers are 100% coated with metallic silver. The amount of coating may vary from about 5% to about 40% by weight, more preferably from 15% to about 25% by weight. In accordance with the invention, the silver-coated fibers can optionally be mixed with gold, platinum, ferromanganese, copper, zinc or mixtures of these materials.

The silver-coated fibers used in accordance with the present invention should be of sufficient length and thickness to allow homogeneous blending with or dispersal in the non-metallic, water-absorbent material. In addition, the percentage of the actual fiber coated with silver is variable and can be modified to alter the blending characteristics of the silver-coated fiber and the eventual water absorbency of the resulting textile matrix. Preferred parameters for the silver-coated fibers are set forth in Table 1 below. One skilled in the art following the teachings of the invention can easily ascertain these parameters.

TABLE 1

|  | Length (Inches) | Denier (dpf) | Silver (% w/w) |
|---|---|---|---|
| Preferred | 0.5-8 | 0.5-50 | 3-75% |
| More Preferred | 0.75-6 | 0.75-6 | 9-60% |
| Most Preferred | 1-3 | 1-10 | 12-30% |

Non-metallic, water-absorbent materials to be used in accordance with the invention include any water-absorbent material that does not exhibit toxicity or immunogenicity to mammals. Preferred water-absorbent materials to be used include polysaccharides due to their water absorbency, lack of toxicity and biodegradability. Although not required for most applications, materials that are bioabsorbable can be used in applications involving implatation. One preferred class of polysaccharides are hydrocolloids such as alginic acids and salts thereof, guar gum, locust bean gum (LBG), pectin, gelatin, xanthan and/or gum karaya, and chitosan. Cellulose derivatives (e.g. salts of carboxymethylcellulose such as sodium carboxymethylcellulose, methylcellulose and hydroxypropylmethylcellulose), as well as hyaluronic acid and its salts, can also be used. Examples of alginic acid salts (i.e., metal alginates) to be used include, but are not limited to, calcium alginate and sodium alginate or combinations thereof. Reference to "water-absorbent" in this context means that the material absorbs at least 25 grams of deionized water per gram of material. However, as will be apparent to those skilled in the art, water-absorbent polysaccharide materials such as metal alginates can easily absorb 60 to 200 times their weight in water.

The water-absorbent materials are in any form that can be readily incorporated into a wound dressing. Examples include, but are not limited to, gels, hydrogels, fibers, or any combination thereof. Preferably, the water-absorbent materials are provided as fibers with alginate fibers such as calcium alginate being especially preferred. One particular example of alginate fibers to be used is calcium alginate fibers co-spun with non-alginate water-absorbent materials such as carboxymethylcellulose "CMC." Such fiber are described in U.S. Pat. No. 6,080,420 assigned to Advanced Medical Solutions Limited, United Kingdom, which is incorporated herein by reference. Another source of calcium alginate fibers is FMC Biopolymer located in Philadelphia, Pa. Preferably, the fibers range in length from 0.5 to 8 inches, with 1 to 3 inches being more preferred.

As previously described, the textile matrix of the invention includes a mixture or blend of the metallic silver-coated fibers with the water-absorbent material. Preferably, the two components are in a substantially homogenous mixture (i.e., intimately blended) to provide uniform absorption of wound exudate and uniform release of silver ions to the wound. The textile matrix is preferably prepared with a thickness of about $\frac{1}{16}$-2 inches thick to facilitate incorporation into wound dressings. The non-woven textile matrix can be cut to any shape or size particularly suitable for end use. Likewise, a sliver can be prepared for use in wound dressings. Reference to a "sliver" means a continuous strand of loosely assembled fibers without twist. The sliver is delivered by the card, the comber, or the drawing frame. The production of a sliver is usually the first step in a textile operation bringing staple fiber into a form that can be drawn (or reduced in bulk) and eventually twisted into a spun yarn. Preferred parameters for blending the textile matrix from the silver coated fibers and the water-absorbent materials are set forth in Table 2 below.

TABLE 2

| | Silver-Coated Fiber (% w/w) | Water-Absorbent (% w/w) |
|---|---|---|
| Preferred | 1-80 | 10-80 |
| More Preferred | 20-70 | 20-70 |
| Most Preferred | 30-60 | 30-60 |

The textile matrix of the invention is prepared using any technique known in the art for blending fibers. Preferably, the textile matrix of the invention is prepared in the following manner when blended with water-absorbent fibers such as calcium alginate:
(a) carding the fibers;
  (i) opening the fibers;
  (ii) blending and orienting the fibers;
(b) cross-lapping the fibers to form a web; and optionally
(c) needle punching the web.

As will be apparent to those skilled in the art, the manufacture of a sliver requires a slight modification of above procedure as is described below:
(a) carding the fibers;
  (i) opening the silver-coated fiber;
  (ii) blending and orienting the fibers;
(b') drawing the fibers; and optionally
(c') roving to further condense the fibers.

The techniques for each of these steps are well know in the art. Descriptions of these techniques can be found in "Wellington Sears Handbook of Industrial Textiles," Earnest R. Kaswell, Wellington Sears Company, Inc. (1963).

Silver-coated fibers to be used in accordance with the invention are preferably obtained as continuous filament fibers which are then cut into short segments having the lengths described above. It has been surprisingly found that the use of cut fiber, rather than staple fiber (which is manufactured in the form of short pieces of fiber), dramatically improves the properties of the final product. This is believed to be due to the substantial lack of or omission of fibers being entangled with each other which is obtained using cut fiber rather than staple fiber. Entangled fibers (i.e., fibers clumped with other fibers) require opening to separate the fibers from each other. Preferably, the cut fiber contains less than 50 percent by volume of entangled fibers, with less than about 30 percent by volume being more preferred, and less than about 10 percent by volume being even more preferred.

The cut fibers are significantly easier to utilize in the manufacturing process due to less clumping (i.e., adhesion of the fibers to each other). While not wishing to be limited by theory, it is believed that this improvement is facilitated by the general axial alignment of the fibers after the continuous filament fibers are cut. This is contrary to the random orientation of the fibers that are obtained from use of the silver-coated staple product.

Carding of the silver-coated fibers is accomplished using any traditional carding process. A preferred carding machine is the Bematic card, manufactured by Bettarini & Serafini S.r.l. (Prato, Italy). Carding blends the fibers together and orients them in generally the same direction, i.e., generally parallel. In the first sub-step of the carding process, the silver-coated fibers are opened. Typically, when the silver-coated fibers are processed wet and subsequently dried, the fibers clump together (though not to the same extent as staple fiber that has been processed and dried). The fibers are opened, typically twice, as needed, to separate the individual fibers from each other to enable them to be blended with the water-absorbent fibers such as calcium alginate fibers. Once opened, the silver-coated fibers and the water-absorbent fibers are then blended and oriented to create a web.

The fibers are cross-lapped to provide substance and rigidity to the web and to optimize surface area of the silver-coated fibers. Preferably, the fibers cross-lapped about 8 or 9 times. The actual amount of cross-lapping needed for any particular web can easily be ascertained by one skilled in the art. An example of equipment that can be used for cross-lapping is manufactured by AUTEFA Automation GmbH in Germany.

In a more preferred embodiment of the invention, the web is needle-punched to interlace and interlock the fibers together. The needle-punched web may then be incorporated into any of a wide variety of wound care products, such as wound dressings, to provide absorbent and antibiotic properties to the product. Needle-punching is not required to obtain the textile matrix, but is preferred for applications that require increased durability of the matrix.

As previously described, preparation of a sliver in accordance with the invention necessitates that the blend of the silver-coated and absorbent fiber be drawn. Drawing of the fibers is accomplished by any technique known in the art. For example, the sliver can be processed through drawframe equipment (such as that made by Reiter Corp., Spartanburg, S.C.) in order to reduce the bulk of the sliver by compacting it.

In a more preferred embodiment of the invention, the sliver is subjected to a roving process to further condense the fibers of the silver. As is known in the art, roving is a condensed sliver that has been drafted, twisted, doubled, and redoubled. The advantages of roving include higher strength and elongation.

The textile matrix of the invention can also include additional fibers, excipients (e.g., binders) and other therapeutic actives such as additional anti-microbial, anti-bacterial, and/or anti-fungal chemical entities or metallic elements such as copper or zinc. Examples of other fibers to be used in accordance with the invention include, but are not limited to, cotton, cellulose, polyester, acrylic, nylon or combinations thereof. One example of an antibiotic to be used is doxycycline. In another embodiment, the textile matrix can also include hormones (e.g., estrogen) to facilitate wound healing. Others examples of antibiotics and hormones to be used in conjunction with the textile matrix of the invention is described in U.S. Pat. No. 5,914,124, which is incorporated herein by reference. In one preferred embodiment, the textile matrix includes silver-coated fibers and either copper- or zinc-coated fibers or a combination of both. However, the use of fibers other than the silver-coated and water-absorbent fibers is preferably less than 40 percent by weight of the matrix to avoid diminishing the antibiotic activity and absorptive qualities of the textile matrix.

The antibiotic properties of the textile matrix are characterized by antimicrobial efficacy, which is determined using the either (1) Dow Corning Shake Flask Test over 24 hours or (2) the New York State 63 Test for Bacteriostatic Activity. In accordance with the invention, the textile matrix exhibits a kill rate of at least 70%, with at least about 85% being more preferred, and at least about 95% being even more preferred. In fact, as demonstrated by the examples, the textile matrix of the invention can exhibit kill rates of 99.9%. One skilled in the art following the teachings of the invention can easily determine these parameters.

The overall absorbency of the textile matrix of the invention is determined using the British Pharmacopoeia test for absorbency of alginate dressings, which is well known in the art. The textile matrix preferably exhibits an absorbency of at least 10 grams of water per gram of matrix (g/g), with at least about 14 g/g being more preferred, and at least about 16 g/g being even more preferred. Water absorbency of the textile matrix facilitates maintaining a moist wound environment while at the same inhibiting unwanted bacterial growth.

While wishing not to be limited by theory, it is believed that the beneficial wound healing characteristics of the textile matrix is due to its combined antibiotic and water-absorbent properties. It known in the art that silver kills bacteria that secrete proteolytic enzymes such as matrix metalloproteinases (MMPs) at the wound site. It is believed that wound healing is often delayed due to an excess of MMPs secreted by bacteria. Some bacterial species, such as Pseudomonas aeruginosa, are in fact known to release significant amounts of MMPs. Likewise, an excess reduction of MMPs may also interfere with the wound healing process. Accordingly, the textile matrix of the invention advantageously provides sustained silver delivery in addition to water-absorbency thereby killing enzyme producing bacteria and removing by absorption wound exudate containing these proteolytic enzymes.

The textile matrix of the invention is useful for any use in which the characteristics of absorption and antimicrobial activity are desired. Accordingly, the present invention also provides wound dressings incorporating the textile matrix to facilitate a moist environment conducive to healing while inhibiting bacterial growth. A cross-sectional view of a representative wound dressing is depicted in FIG. 1. FIG. 1 depicts a bandage 10 including a flexible backing layer 12 having disposed on one side a sliver of textile matrix 14. Backing layer 12 also includes adhesive coatings 16 disposed on the same side as sliver 14 but not encompassing sliver 14. Backing layer 10 is made from any flexible material known in the art for wound dressings. Preferably, the material for backing layer 10 is water impermeable while at the same time gas permeable. Skin compatible adhesives for adhesive coatings 16 are also well known in the art.

The wound dressings of the invention due to the textile matrix of the invention are capable of absorbing wound exudate and inhibiting wound infection due to bacteria. They are useful in treating a wide variety of wounds and burns, from minor abrasions to traumatic wounds, and are especially useful in the treatment of chronic wounds, such as leg ulcers, pressure sores, cavity wounds and donor sites. The wound dressings of the invention are also particularly useful for the management of acute traumatic wounds Moreover, wound dressings incorporating the textile matrix exhibit increased comfort to the wearer as compared to current silver-coated fiber bandages. The increased comfort is due in part to the increased flexibility offered by the textile matrix, which can be described as silky to the touch. In addition, the textile matrix of the invention reduces physical adherence of the dressing to the wound as compared to dressings containing water-absorbent material only. The reduced adhesion is attributed to the silver-coated fibers in the matrix that is hydrophobic. This reduced adherence renders the wound dressings of the invention more comfortable to wear, and decreases pain and discomfort when removed.

EXAMPLES

Example 1

Four (4) textile matrix web samples were manufactured using continuous filament silver-plated nylon fibers of approximately 3 denier per filament ("dpf") cut to approximately 2 inches in length. The silver content of the cut fibers was approximately 21 percent by weight. The cut fibers were blended with CMC-calcium alginate fibers from Advanced Medical Solutions to provide homogenous mixture of fibers. The CMC-calcium alginate fibers were an average of approximately 2 inches in length. The textile matrix samples contained percentages by weight of silver/alginate fibers (0/100, 20/80, 50/50, and 70/30).

Absorbency was tested as using the British Pharmacopoeia test for absorbency of alginate dressings. A weighted 5-cm×5-cm specimen of each of the textile matrix samples was placed in a petri dish. A sample of a CMC-calcium alginate matrix (i.e., devoid of silver fibers) from Advanced Medical Solutions ("ADMEDSOL") was used as a control since it is representative of an untreated wound care product. A volume of sodium chloride and calcium chloride solution, previously warmed to 37° C., corresponding to 40 times the weight of the material being examined to the nearest 0.5 mL was added, and allowed to stand for 30 minutes at 37° C. Using forceps, the textile matrix was then suspended by a corner for 30 seconds, and the sample was weighed. The experiment was repeated for 10 samples. The results are set forth in the table 3 below as average weight of solution retained per 100 cm$^2$.

The samples were also tested for antimicrobial activity using the NY State 63 Test for Bacteriostatic Activity. Five 1" squares of the textile matrix were used as sample. Five 1" squares of CMC-calcium alginate material were used as controls. Samples and controls were sterilized. Ten bottom sections of 35×10-mm disposable tissue culture dishes were placed in standard petri dishes containing 10 ml of sterile distilled water. 0.2 ml of a 24 hour broth culture containing 105 organisms was placed in the center of each disposable tissue culture dish. The test and control squares were then placed in the disposable tissue culture dishes, with one side in contact with the inoculum. The covers were then replaced on the standard petri dishes. The petri dishes were then placed on a level shelf of an incubator at 37° C. and incubated for 24 hours. After 24 hours, the samples were removed from the petri dishes by means of a flamed forceps and placed into 100 ml of Letheen broth in an 8-oz. wide mouth jar. The jar was shaken vigorously for about 1 minute. Serial dilutions were made and placed on AATCC bacteriostasis agar. Plates containing the agar were then incubated for 24-48 hours at 37° C. The percentage reduction of inoculum by the samples and controls was calculated. Antimicrobial activity of the samples was calculated and the results are also listed in the table 3 below.

TABLE 3

| Silver (Percentage by Weight) | Alginate (Percentage by Weight) | Antimicrobial Activity (Kill %) | Absorption (g/g) |
| --- | --- | --- | --- |
| 0 | 100 | 0% | 19.6 |
| 20 | 80 | >99.9% | NM* |
| 50 | 50 | >99.9% | 18.2 |
| 70 | 30 | >99.9% | 17.8 |
| 80 | 20 | >99.09% | NM* |

*Not Measured

As can be seen from the foregoing results, the textile matrix samples exhibited a surprising retention of absorption capacity, even with the samples containing a majority of hydrophobic silver-coated fibers. For example, the 50/50% blend sample exhibited an absorption rate approximately 7 percent less than the control ((19.6 g/g-18.2 g/g)/ 19.6·100%). Such a low reduction in absorption was considered surprising when a 50% reduction would have ordinarily been expected.

Example 2

A textile matrix sample containing the 50/50 blend as described in Example 1 was tested for antimicrobial activity using the Dow Corning Corporate Test Method 0923. One 3" square of the textile matrix was used as sample (i.e., test sample). One 3" square of the 100% CMC-calcium alginate was used as a control (i.e., control sample). Test and control textile samples were sterilized using. Two 250 ml screw cap Erlenmeyer flasks containing 70±0.01 ml of a sterile buffer solution were inoculated with 5±0.01 ml of an 18 hour broth culture containing 1.5-3.0×10$^5$ organisms and shaken vigorously for about 1 minute to provide a homogenous suspension. Each flask is considered to be at "0" contact time. Duplicate "0" time plating samples were immediately prepared by serial dilution of the suspension and 1±0.01 ml of each duplicate sample placed in a petri dish, suspended by adding about 16 ml of Tryptone Glucose Extract agar, and incubated at 37° C.

Immediately following preparation of "0" time plating samples, the test and control textile samples were placed in their individual flasks and shaken vigorously for about 1 hour. Each flask is considered to be a 1-hour contact time. Duplicate plating samples were immediately prepared by serial dilution, and plated as described above for the "0" time samples.

The petri dishes from both test and control samples were incubated at 37° C. for 24 to 36 hours and the percentage reduction of inoculum by test and control samples determined. Antimicrobial activity of the samples was calculated and the results are listed in the table 4 below.

TABLE 4

| Sample | Organism Count (CFU/mL) | | |
|---|---|---|---|
| | "0" Time | 1-Hour | Percent Reduction |
| 50/50 Blend | 18,000 | 850 | 95.00 |
| ADMEDSOL Calcium Alginate | 16,000 | 19,000 | — |

As can be seen from the foregoing results, the textile matrix of the invention provided excellent antimicrobial activity, which is attributed to the silver-coated fibers, dispersed throughout the matrix.

We claim:

1. A hydrophilic textile matrix having antibiotic activity, said matrix being a non-woven material comprising a blend of metallic silver-coated fibers and non-metallic, water-absorbent material,
   wherein said non-metallic, water-absorbent material is in the form of a hydrogel.

2. The textile matrix of claim 1, wherein said matrix has a water absorption of at least about 10 grams per gram of matrix.

3. The textile matrix of claim 2, wherein said water absorption is at least about 14 grams per gram of matrix.

4. The textile matrix of claim 3, wherein said water absorption is at least about 16 grams per gram of matrix.

5. The textile matrix of claim 1, wherein said metallic silver-coated fibers are about 0.5 to about 50 denier per filament.

6. The textile matrix of claim 5, wherein said metallic silver-coated fibers are about 0.7 to about 30 denier per filament.

7. The textile matrix of claim 6, wherein said metallic silver-coated fibers are about 1 to about 10 denier per filament.

8. The textile matrix of claim 1, wherein said blend comprises about 1 to about 80 percent by weight of said metallic silver-coated fibers and about 10 to about 80 percent by weight of non-metallic, water-absorbent fibers.

9. The textile matrix of claim 8, wherein said blend comprises about 20 to about 80 percent by weight of said metallic silver-coated fibers and about 20 to about 80 percent by weight of non-metallic, water-absorbent fibers.

10. The textile matrix of claim 9, wherein said blend comprises about 30 to about 70 percent by weight of said metallic silver-coated fibers and about 30 to about 70 percent by weight of non-metallic, water-absorbent fibers.

11. A hydrophilic textile matrix having antibiotic activity, said matrix being a non-woven material comprising a blend of metallic silver-coated fibers and non-metallic, water-absorbent material,
   wherein said non-metallic, water-absorbent material is selected from an alginic acid or salt thereof, guar gum, locust bean gum, pectin, gelatin, xanthan gum, gum karaya, chitosan, hyaluronic acid and salts thereof, cellulose derivatives, or a salt of carboxymethylcellulose.

12. The textile matrix of claim 11, wherein the non-metallic, water-absorbent material comprises a hydrocolloid that is an alginate or derivative thereof.

13. The textile matrix of claim 11, wherein said matrix has a water absorption of at least about 10 grams per gram of matrix.

14. The textile matrix of claim 13, wherein said water absorption is at least about 14 grams per gram of matrix.

15. The textile matrix of claim 14, wherein said water absorption is at least about 16 grams per gram of matrix.

16. The textile matrix of claim 11, wherein said metallic silver-coated fibers are about 0.5 to about 50 denier per filament.

17. The textile matrix of claim 16, wherein said metallic silver-coated fibers are about 0.7 to about 30 denier per filament.

18. The textile matrix of claim 17, wherein said metallic silver-coated fibers are about 1 to about 10 denier per filament.

19. The textile matrix of claim 11, wherein said blend comprises about 1 to about 80 percent by weight of said metallic silver-coated fibers and about 10 to about 80 percent by weight of non-metallic, water-absorbent material.

20. The textile matrix of claim 19, wherein said blend comprises about 20 to about 80 percent by weight of said metallic silver-coated fibers and about 20 to about 80 percent by weight of non-metallic, water-absorbent material.

21. The textile matrix of claim 20, wherein said blend comprises about 30 to about 70 percent by weight of said metallic silver-coated fibers and about 30 to about 70 percent by weight of non-metallic, water-absorbent material.

22. A hydrophilic textile matrix having antibiotic activity, said matrix being a non-woven material comprising a blend of metallic silver-coated fibers and non-metallic, water-absorbent material,
  wherein said non-metallic, water-absorbent material is calcium alginate, sodium alginate, or a derivative thereof.

23. The textile matrix of claim 22, wherein said matrix has a water absorption of at least about 10 grams per gram of matrix.

24. The textile matrix of claim 23, wherein said water absorption is at least about 14 grams per gram of matrix.

25. The textile matrix of claim 24, wherein said water absorption is at least about 16 grams per gram of matrix.

26. The textile matrix of claim 22, wherein said metallic silver-coated fibers are about 0.5 to about 50 denier per filament.

27. The textile matrix of claim 26, wherein said metallic silver-coated fibers are about 0.7 to about 30 denier per filament.

28. The textile matrix of claim 27, wherein said metallic silver-coated fibers are about 1 to about 10 denier per filament.

29. The textile matrix of claim 22, wherein said blend comprises about 1 to about 80 percent by weight of said metallic silver-coated fibers and about 10 to about 80 percent by weight of non-metallic, water-absorbent material.

30. The textile matrix of claim 29, wherein said blend comprises about 20 to about 80 percent by weight of said metallic silver-coated fibers and about 20 to about 80 percent by weight of non-metallic, water-absorbent material.

31. The textile matrix of claim 30, wherein said blend comprises about 30 to about 70 percent by weight of said metallic silver-coated fibers and about 30 to about 70 percent by weight of non-metallic, water-absorbent material.

32. A wound dressing comprising a flexible backing material and a layer of a hydrophilic textile matrix having anti-microbial activity disposed on one side of said backing material, said matrix comprising a non-woven material including a blend of metallic silver-coated fibers and a non-metallic, water-absorbent material;
  wherein said non-metallic, water-absorbent material is selected from a hydrogel, a hydrocolloid, or calcium alginate or a derivative thereof.

33. The wound dressing of claim 32, wherein said backing layer includes an adhesive layer disposed on the same side as said hydrophilic textile matrix but excluding said hydrophilic textile matrix.

* * * * *